(12) United States Patent
Ling

(10) Patent No.: US 12,121,892 B2
(45) Date of Patent: Oct. 22, 2024

(54) APPARATUS AND METHOD FOR COLLECTING AND TESTING SAMPLE

(71) Applicant: Assure Tech. (Hangzhou) Co., LTD, Hangzhou (CN)

(72) Inventor: Shisheng Ling, Hangzhou (CN)

(73) Assignee: Assure Tech. (Hangzhou) Co., LTD, Hangzhou (CN)

( * ) Notice: Subject to any disclaimer, the term of this patent is extended or adjusted under 35 U.S.C. 154(b) by 889 days.

(21) Appl. No.: 17/170,928

(22) Filed: Feb. 9, 2021

(65) Prior Publication Data

US 2022/0250053 A1    Aug. 11, 2022

(51) Int. Cl.
 *B01L 1/00*    (2006.01)
 *B01L 3/00*    (2006.01)
 *B01L 3/02*    (2006.01)

(52) U.S. Cl.
 CPC ............. *B01L 3/5023* (2013.01); *B01L 3/021* (2013.01); *B01L 2200/026* (2013.01); *B01L 2200/0689* (2013.01); *B01L 2200/085* (2013.01); *B01L 2200/10* (2013.01); *B01L 2300/0672* (2013.01); *B01L 2300/069* (2013.01); *B01L 2300/0877* (2013.01)

(58) Field of Classification Search
 None
 See application file for complete search history.

(56) References Cited

U.S. PATENT DOCUMENTS 11,630,036 B2 *   4/2023   Ling   .................. B01L 3/502
                                                    422/68.1

* cited by examiner

*Primary Examiner* — Jyoti Nagpaul
(74) *Attorney, Agent, or Firm* — Bayramoglu Law Offices LLC

(57) ABSTRACT

An apparatus for collecting and testing a sample is provided. The apparatus includes a test cavity and a collecting component. The test cavity is connected to the collecting component and the test cavity and the collecting component are in a liquid communication. An inner wall of the test cavity is provided with a first step. The collecting component includes a collecting rod and an absorbing element sleeved on the collecting rod. A connecting end of the collecting rod is provided with a barb. A tail end of the barb is tapered. The barb at the connecting end is clamped to the first step to connect the test cavity with the collecting component. A collecting and testing apparatus with an integrated structure is provided. The integrated structure integrates the collection and test of a sample, reduces a product structure and an operation difficulty of subjects.

12 Claims, 4 Drawing Sheets

APPARATUS AND METHOD FOR COLLECTING AND TESTING SAMPLE

TECHNICAL FIELD

The present invention relates to a sample collecting; component and an apparatus for collecting and testing a sample, and particularly to a collecting and testing apparatus and method for collecting a fluid sample and mixing the sample with a buffer solution followed by testing.

BACKGROUND

The following background art is used to help the reader understand the present invention, and should not be considered as the prior art.

The technology of testing the presence of an analyte in a sample using the principle of an immunological binding reaction has been widely used in various fields. This technology can be used to test analytes in various biological samples (saliva, blood, urine, serum, sweat, etc.) to monitor diseases and human health (early pregnancy, tumors, infectious diseases, drugs, etc.). The fundamental principle of this test technology is based on the properties of specific binding between immune molecules, such as antibodies and antigens, haptens/antibodies, biotin and antibiotin.

In the field of medical diagnosis, it is a relatively common method to collect a test liquid sample with a testing apparatus or a testing cup and determine whether the liquid sample contains an analyte. Such a testing apparatus or a testing cup generally requires that a sample is collected in a sample container, and a related technician inserts a test reagent strip with a part of the reagent strip immersed in the sample, takes the reagent strip out after certain time, and reads the test result.

US patents US2004/0184954 and US2004/0237674 disclose some apparatuses for collecting saliva and testing whether the saliva contains illegal pharmaceutical ingredients. The two patents provide apparatuses and methods for collecting and testing saliva. In these apparatuses, after a sample is sampled on a collector, the sample in an absorbing component on the collector is squeezed into a collection cavity by applying an external force, and then tested.

However, the existing testing apparatuses have the following problems:
1. A sufficient amount of samples is required. Most of the samples are collected to test illegal drugs or drugs of abuse, and the subjects do not cooperate; or the sample sizes of the subjects are too small, for example, a little saliva is collected, and sometimes, a lot of analytes in the samples need to be tested at the same time, which requires even more samples.
2. Most of the testing apparatuses are of split structures and are operated separately. The operation requirements are relatively high.
3. The structures of the testing apparatuses are not small enough to be portable.

SUMMARY

The present invention provides a collecting and testing apparatus with an integrated structure, which can integrate the collection and test of a sample, reduces the product structure and the operation difficulty of subjects, allows an operator to contact the sample as little as possible, reduces the chance of infection; and improves operator safety. In addition, the use of the testing apparatus for testing greatly reduces the sample demand, and is more conducive to the success of test.

Specifically; the present invention provides an apparatus for collecting and testing a sample, the apparatus includes a test cavity and a collecting component, the test cavity is connected to the collecting component and the two are in liquid communication; an inner wall of the test cavity is provided with a first step, the collecting component includes a collecting rod and an absorbing element sleeved on the collecting rod; a connecting end of the collecting rod is provided with a barb, and a tail end of the barb is tapered; and the barb at the connecting end is clamped to the first step to connect the test cavity with the collecting component.

In some preferred embodiments, the connecting end of the collecting rod of the collecting component is inserted into the test cavity from a bottom of the test cavity, the tail end of the barb at the connecting end enters the test cavity, then an open end of the barb is compressed, and the barb and the connecting end enter the test cavity; and after the open end of the barb reaches the first step, because the inner diameter of the test cavity increases, the open end of the barb rebounds to restore to the original shape, and the barb is clamped to the first step.

In some preferred embodiments, the collecting rod is provided with at least two ribs, and a diversion trench is formed between the ribs; and liquid on the absorbing element is communicated with the test cavity through the diversion trench.

In some preferred embodiments, the rib is of a stepped structure; and the absorbing element is located on an upper step.

In some preferred embodiments, a conical lug is provided on the collecting rod adjacent to a collecting end of the absorbing element.

In some preferred embodiments, the apparatus for collecting and testing a sample further includes a cover that covers the test cavity, and a clamping groove for accommodating the test element is provided in the cover.

In some preferred embodiments, the inner wall of the test cavity is further provided with a second step above the first step.

In some preferred embodiments, the apparatus for collecting and testing a sample further includes a cushion; and the cushion is located on the second step. The function of the cushion is to prevent a large amount of liquid on the absorbing element from being flushed too violently to the test cavity and the test element in the test cavity, and the cushion plays a buffering role.

In some preferred embodiments, the liquid that enters the test cavity through the diversion trench of the collecting rod first flows into the cushion, and then flows from the cushion to the test element.

In some preferred embodiments, the apparatus for collecting and testing a sample further includes a buffer cavity, a sealing sheet for sealing the buffer cavity, and a pipetting cavity hermetically connected to the buffer cavity; and a buffer solution is sealed in the buffer cavity. In some embodiments, the sealing sheet is an aluminum foil.

In some preferred embodiments, a sealing gasket is arranged on an outer wall of the bottom of the test cavity, and the collecting component and the test cavity enter the pipetting cavity to form a seal between the test cavity and the pipetting cavity.

In some preferred embodiments, the collecting component connected to the test cavity is inserted into the pipetting cavity; first, the absorbing element of the collecting component is located directly above an opening of the pipetting cavity; second, the collecting component continues to move in a direction of insertion into the pipetting cavity, and the test cavity enters the pipetting cavity to form a seal; third, the collecting component continues to move in the direction of insertion into the pipetting cavity, and the conical lug of the collecting rod contacts the sealing sheet; finally, the collecting component continues to move in the direction of insertion into the pipetting cavity, the conical lug of the collecting rod reaches the bottom of the buffer cavity, the conical lug of the collecting rod pierces the sealing sheet, the absorbing element enters the buffer cavity, and the buffer solution enters the absorbing element to be mixed with a sample on the absorbing element; and the mixed liquid flows into the test cavity through the absorbing element along the diversion trench of the collecting rod.

In some preferred embodiments, the test cavity is transparent or is provided with a transparent window.

In some preferred embodiments, there may be one or a plurality of test elements. The plurality of test elements may be used to test different analytes in the sample.

In some preferred embodiments, the buffer cavity is in threaded connection with the pipetting cavity.

In some preferred embodiments, the cushion is in contact with the test element.

In some preferred embodiments, the cover is screwed to cover the test cavity.

On the other hand, the present invention further provides a method for collecting and testing a liquid sample, using the apparatus for collecting and testing a sample, wherein the apparatus includes a test cavity and a collecting component, the test cavity is connected to the collecting component and the two are in liquid communication; an inner wall of the test cavity is provided with a first step, the collecting component includes a collecting rod and an absorbing element sleeved on the collecting rod; a connecting end of the collecting rod is provided with a barb, and a tail end of the barb is tapered; the barb at the connecting end is clamped to the first step to connect the test cavity with the collecting component; the collecting rod is provided with at least two ribs, and a diversion trench is formed between the ribs; the apparatus for collecting and testing a sample further includes a buffer cavity, a sealing sheet for sealing the buffer cavity, and a pipetting cavity hermetically connected to the buffer cavity; a buffer solution is sealed in the buffer cavity, wherein the method includes:

collecting a sample with the collecting component and filling the absorbing element with the liquid sample;

inserting the collecting component filled with the liquid sample and the test cavity connected to the collecting component into the pipetting cavity;

moving the collecting component in the pipetting cavity in a direction of insertion into the pipetting cavity, so that the collecting component reaches the sealing sheet;

enabling the collecting component to pierce the sealing sheet on the buffer cavity and enter the buffer cavity to mix the sample on the absorbing element with the buffer solution;

guiding the mixed liquid to flow onto the test element in the test cavity along the absorbing element and the diversion trench for testing;

and reading the test result on the test element.

In some preferred embodiments, a conical lug is provided on the collecting rod adjacent to a collecting end of the absorbing element; and the sealing sheet is pierced by the conical lug.

In some preferred embodiments, the apparatus for collecting and testing a sample further includes a cover that covers the test cavity, and a clamping groove for accommodating the test element is provided in the cover, wherein after the cover covers the test cavity, the test element is located in the test cavity.

In some preferred embodiments, the apparatus for collecting and testing a sample further includes a cushion; a second step is provided in the test cavity; the cushion is located on the second step; and the liquid that enters the test cavity through the diversion trench of the collecting rod first flows into the cushion, and then flows from the cushion to the test element.

In some preferred embodiments, a sealing gasket is arranged on an outer wall of the bottom of the test cavity, and after the collecting component and the test cavity enter the pipetting cavity, a seal is formed between the test cavity and the pipetting cavity.

The present invention further provides a sample collecting component connected to a testing apparatus. Through the collecting component of this structure, the testing apparatus can be of an integrated structure, which not only reduces the size of the testing apparatus, but also realizes integrated test, and is convenient to operate.

In a specific technical solution, the present invention provides a sample collecting component connected to a testing apparatus, including a collecting rod and an absorbing element with a cavity, and the absorbing element is sleeved on the collecting rod through the cavity; the collecting rod is provided with at least two ribs, and a diversion trench is formed between the ribs.

In some preferred embodiments, the rib is of a stepped structure; and the absorbing element is located on the steps.

In some preferred embodiments, a conical lug is provided on the collecting rod adjacent to a collecting end of the absorbing element.

In some preferred embodiments, a connecting end of the collecting rod is provided with a barb, and a tail end of the barb is tapered.

The apparatus for collecting and testing a sample according to the present invention realizes the functions of sample collection, slow release and detection through the integrated structure of the collecting component, the test cavity and the buffer cavity. First, the operation of the testing apparatus is easy, which reduces the using difficulty of an operator. Second, the lumber and time that the operator contacts with the sample are effectively reduced, the probability that the operator is infected is reduced, the operator's safety is ensured, and the apparatus is particularly suitable for HIV test. Third, the integrated testing apparatus is filled with a buffer solution, so that the collection amount of a sample is small, and the collection amount is optimized from milliliters to microliters. Finally, due to the integrated structure, the collection, slow release and test are realized in one step, which improves the success rate of test.

REFERENCE SIGNS

Figure 1:
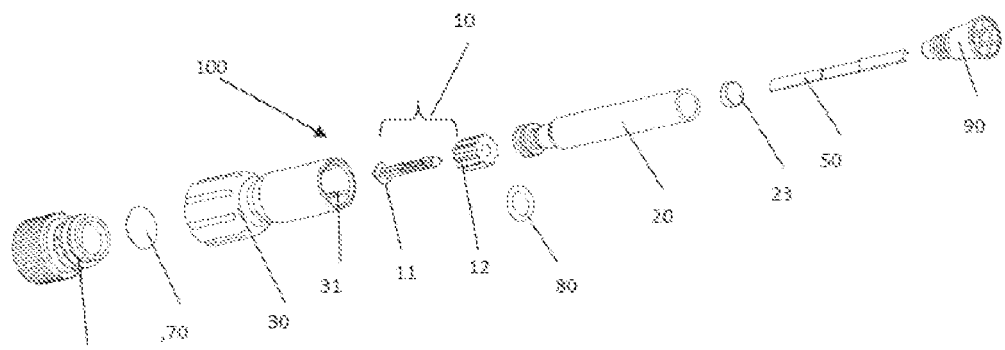
FIG. 1 is an exploded schematic diagram of an apparatus for collecting and testing a sample according to the present invention.
Figure 2:
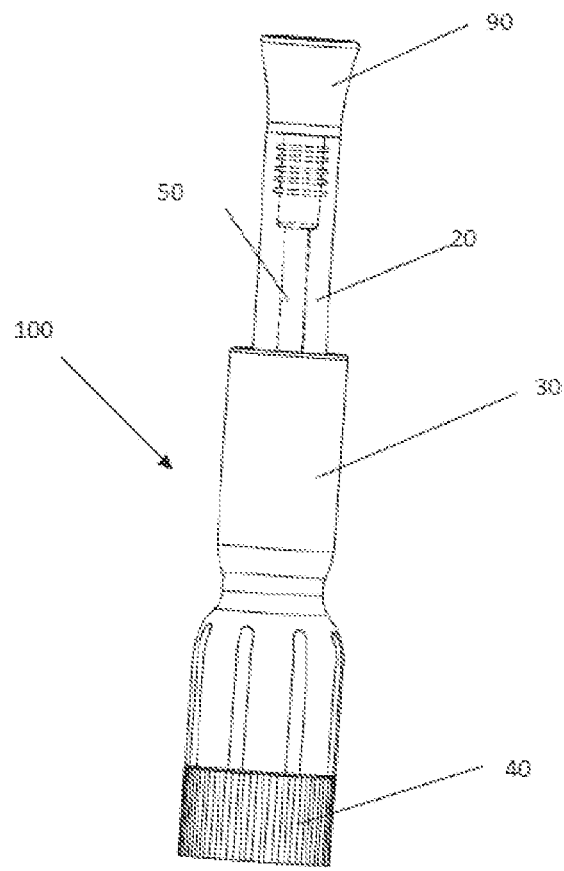
FIG. 2 is a schematic diagram of the apparatus for collecting and testing a sample according to the present invention.
Figure 3:
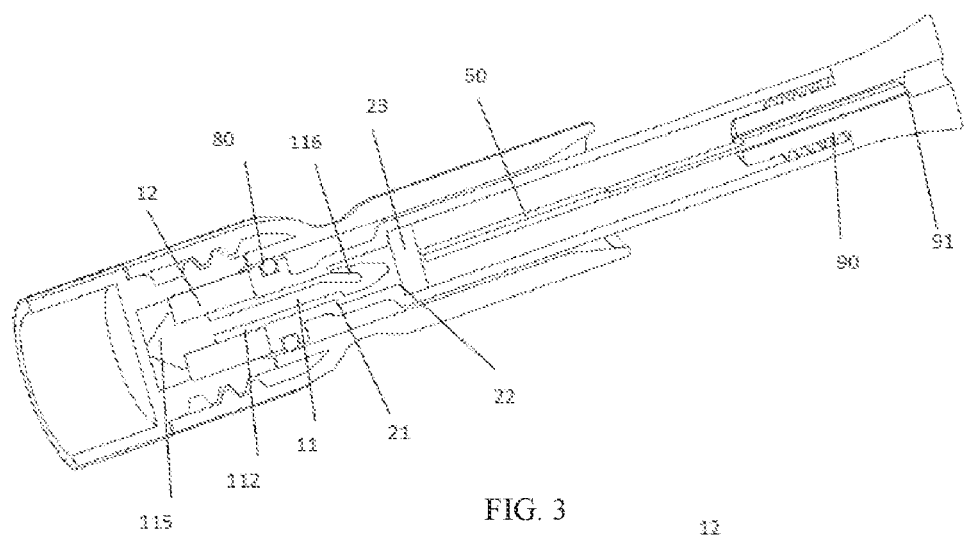
FIG. 3 is a cross-sectional view of the apparatus for collecting and testing a sample according to the present invention.

Apparatus 100 for collecting and testing a sample, sample collecting component 10, collecting rod 11, rib 111, diversion trench 112, upper step 113, lower step 114, conical lug 115, barb 116, connecting end 117 of the collecting rod, collecting end 118 of the collecting rod, absorbing element 12, absorbing element cavity 121, test cavity 20, first step 21, second step 22, cushion 23, pipetting cavity 30, clip 31, buffer cavity 40, test element 50, buffer solution 60, sealing sheet 70, sealing gasket 80, cover 90, cover clamping groove 91.

DETAILED DESCRIPTION OF EMBODIMENTS

The structures or technical terms used in the present invention will be further described below.

Test

Test means to assay or detect the presence of a substance or material, for example, but not limited to, chemicals, organic compounds, inorganic compounds, metabolites, drugs or drug metabolites, organic tissues or metabolites of organic tissues, nucleic acids, proteins or polymers. In addition, the test denotes the amount of the test substance or material. Furthermore, the test also denotes immunoassay, chemical test, enzyme test, etc.

Sample

Samples described in the present invention refer to those substances that can be used to test, assay or diagnose the presence of analytes of interest. The samples may be, for example, liquid samples. The liquid samples may include blood, plasma, serum, urine, saliva and various secretions, and may also include liquid solutions formed after solid samples and semi-solid samples are pretreated. The collected samples can be used for immunoassay, chemical test, enzyme test and other methods to test the presence of analytes. In a preferred embodiment, the samples of the present invention are saliva samples.

Analyte

With the apparatus and method of the present invention, any analyte can be analyzed. Analytes can be tested in any liquid or liquefied samples, such as urine, saliva, blood, plasma, or serum.

Analytes may also be some haptens, including thugs (such as thugs of abuse). "Drugs of abuse" (DOA) refer to drugs for non-medical purposes (usually paralyzing nerves). The apparatus can also be used to test such drugs that have medical purposes but are easily overdosed, such as tricyclic antidepressants (imipramine or analogues) and acetaminophen. After being absorbed by the human body, these drugs are decomposed into different small molecular substances. These small molecular substances are present in body fluids such as blood, urine, saliva and sweat, or in part of the body fluids.

Test Element 50

The test element 50 may be a transverse flow test strip, which can be used to test a variety of analytes. Of course, other suitable test elements may also be used in the present invention. Various test elements may be combined and used in the present invention. One form is test paper. The test paper used to analyze analytes in samples (such as drugs or metabolites indicating physical conditions) may be in various forms, such as immunoassay or chemical analysis. A non-competitive or competitive analysis mode may be used for the test paper. The test paper includes a water absorbing material having a sample receiving zone, a reagent zone, and a test zone. A sample is added to the sample receiving zone and flows to the reagent zone by capillary action.

In the reagent zone, if an analyte is present, the sample is bound to the reagent. The sample then continues to flow to the test zone. Some other reagents, such as molecules specifically bound to the analyte, are immobilized in the test zone. These reagents react with the analyte (if present) in the sample and bind the analyte in the zone, or are bound with one of the reagents in the reagent zone. A marker for displaying a test signal is present in the reagent zone or a separated marker zone.

The typical non-competitive analysis mode is: if the sample contains the analyte, a signal will be generated, and if the sample does not contain the analyte, no signal will be generated. In the competitive method, a signal is generated if the analyte is not present in the sample, and no signal is generated if the analyte is present.

The test element 50 may be test paper made of a material that absorbs water or does not absorb water. The test paper may include a variety of materials for liquid sample delivery. One material of the test paper may cover another material, for example, a filter paper covers a nitrocellulose membrane. One or more materials may be used for one zone of the test paper, and other different one or more materials may be used for another zone. The test paper may be adhered to a support or a hard surface to increase the strength of the test paper held. The analyte is tested by a signal generation system, for example, one signal generation system or a composition of more signal generation systems is immobilized in the analyte test zone of the test paper by using one or more enzymes that specifically react with the analyte, and using the aforementioned method of immobilizing a specific binding substance on a test paper. The substance that generates signals may be on the sample receiving zone 201, the reagent zone, or the test zone, or the entire test paper, and the substance can fill one or more materials of the test paper. A signal substance-containing solution is added to the surface of the test paper or one or more materials of the test paper are immersed in the signal substance-containing solution. The test paper with the signal substance-containing solution added is dried.

The zones of the test paper can be arranged in the following manner: a sample receiving zone, a reagent zone, a test zone, a control zone, a zone for determining whether a sample is adulterated, and a liquid sample absorption zone. The control zone is behind the test zone. All the zones can be arranged on a test paper made of only one material. Different materials may also be used for different zones. Each zone may be in direct contact with a liquid sample, or different zones are arranged according to the direction of flow of the liquid sample, and the end of each zone is connected with and overlaps the front end of another zone.

The materials used may be the ones with good water absorption, such as filter paper, glass fibers or a nitrocellulose membrane. The test paper may also be in other forms.
Test Cavity 20

The test cavity 20 is usually a cavity for receiving the test element 50, and a liquid sample can enter the cavity 20 to contact the test element 50 for test. The test cavity is in various shapes, and can be designed according to the shape and number of the test element 50 to be received. In the present invention, the test element is a test strip 50. Therefore, in one embodiment, the test cavity 20 is of a cylindrical structure, and the test strip 50 is located in the cylinder. In some other embodiments, a cover 90 that seals the upper cavity opening is arranged on the test cavity 20, and the test strip 50 is fixed on the cover 90 and is thus relatively fixedly located in the test cavity 20. In some preferred embodiments, the cylinder 20 has a window, and the window is opposite to the test zone of the test strip to facilitate the observation of the test result of the test strip. Alternatively, in some other embodiments, the cylinder itself is transparent, which facilitates the observation of the test result of the test strip.

In the following detailed description, the reference texts accompanying the legends are a part here, and are described by way of examples to illustrate the specific solutions that may be implemented in the present invention. It is not excluded that the present invention may also be implemented by other specific solutions and the structure of the present invention may be changed without departing from the scope of use of the present invention.

As shown in FIGS. 1, 4 and 6-8, in the present invention, a collecting component 10 includes a collecting rod 11 and an absorbing element 12, wherein the absorbing element is provided with a cavity 121 and sleeved on the collecting rod 11 through the cavity 121. In a specific embodiment, the absorbing element 12 is made of sponge, which has strong liquid absorption ability. More specifically, the sponge is medical sponge.

A rod body of the collecting rod 11 is provided with at least two ribs 111. The ribs 111 are raised on the rod body of the collecting rod 11, so that a diversion trench 112 is formed between the raised ribs 111. The diversion trench 112 is used to guide liquid to flow therein. More specifically, the rib 111 is of a stepped structure, that is, one raised part of the rib 111 is higher than the other raised part. The high raised part is an upper step 113, and the low raised part is a lower step 114. The absorbing element 12 is sleeved on the upper step 113, that is, the upper step 113 of the rib of the collecting rod is in contact with an inner wall of the cavity 121 of the absorbing element, so that the absorbing element 12 is fixed on the collecting rod 11. The lower step 114 of the rib is raised low. When liquid on the absorbing element 12 is squeezed to flow to the diversion trench 112 and flows along the collecting rod 11, liquid communication can be realized between the lower step 114 and the diversion trench 112, which is more conducive to the mixing of the liquid and the circulation of the liquid.

Figure 4:
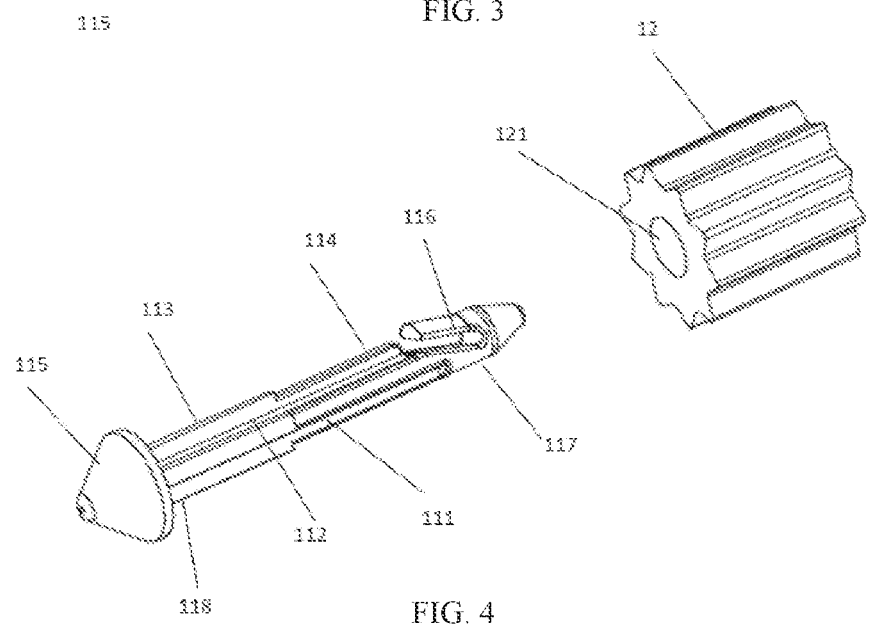
FIG. 4 is an exploded schematic diagram of a sample collecting component in the present invention.

Two ends of the collecting rod 11 are respectively a collecting end 118 and a connecting end 117, wherein the absorbing element 12 is located at the collecting end 118. In one embodiment, a conical lug 115 is provided at an end portion of the collecting end 118. The conical lug 115 can pierce a thin sheet, for example, a metal sheet such as an aluminum foil or a tin foil, or paper, a plastic sheet, or the like. In some other embodiments, a barb 116 is provided at the connecting end 117 of the collecting rod. As shown in FIG. 4, the barb 116 is hollowed out in the middle. When a pressure is applied, an open end of the barb 116 moves toward the hollow part. As a result, the peripheral surface of the entire barb is reduced to facilitate access to a cavity of a certain volume. After the pressure disappears, the open end of the barb 116 returns to its original position. More specifically, a tail end of the barb 116 is tapered, so that the connecting end 117 of the collecting rod can easily enter the cavity.

As shown in FIGS. 1-8, an apparatus 100 for collecting and testing a sample according to the present invention first includes a test cavity 20 and the collecting component 10, and the test cavity 20 is fixedly connected to the collecting component 10. Specifically, the test cavity 20 is of a cylindrical structure. In addition, the inner diameter of the cylinder has a step change and is divided into three different inner diameters. From the bottom to top of the test cavity 20, the inner diameter of the cavity gradually increases stepwise. Therefore, an inner wall of the test cavity 20 has a first step 21 and a second step 22. The connecting end 117 of the collecting component is inserted from a bottom of the test cavity 20. An outer circumference of the barb 116 is larger than an inner circumference of the bottom of the test cavity 20. The barb 116 is compressed, and its open end sinks into the middle cavity, so that the outer circumference of the barb 116 is adapted to the inner circumference of the bottom of the test cavity. After the connecting end 117 enters the test cavity 20 until the entire barb 116 is located at the first step 21, because the inner diameter of the test cavity 20 at the first step increases, the barb 116 is not compressed, and the open end returns to the original position. In this way, the diameter of the entire barb 116 is larger than the inner diameter of the test cavity 20 under the first step 21. Therefore, the barb 116 is clamped to the first step 21, the collecting rod 11 is fixedly connected to the test cavity 20, and the collecting component 10 is also fixedly connected to the test cavity 20.

Figure 5:
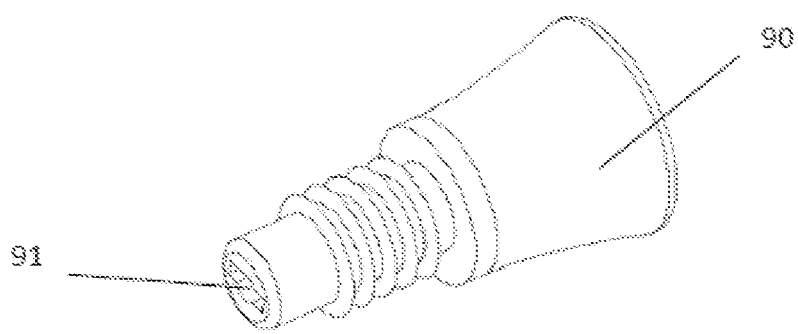
FIG. 5 is a schematic diagram of a cover in the present invention.

A cover 90 is arranged at a top of the test cavity 20, and the cover 90 seals the test cavity 20. In one embodiment, the cover 90 is screwed to cover the test cavity 20. In the present invention, the cover 90 is also used to fix the test element 50. In one embodiment, the test element 50 is a test strip. Specifically, there may be a plurality of test strips for testing different analytes. The cover 90 is provided with a clamping groove 91, as shown in FIG. 5. Of course, there may be a plurality of clamping grooves 91, which are arranged on the cover 90 and used to clamp tail ends of the test strips 50, so that the test strips 50 are fixed on the cover 90. After the cover 90 covers the test cavity 20, the test strip 50 is fixed in the test cavity 20.

A cushion 23 is placed on the second step 22 above the first step 21 in order to allow liquid to slowly flow to the test element 50, that is, the sample zone of the test strip, to prevent excessive liquid from entering the test cavity 20 to submerge the test zone of the test element 50 (test strip), and to ensure the validity of test. In some preferred embodiments, a sample end of the test element 50 is in zero clearance contact with the cushion 23, so as to ensure that the test element 50 absorbs enough liquid to ensure the success rate of the test.

After being squeezed, the liquid on the absorbing element 50 flows into the diversion trench 112, flows into the test cavity 20 through the diversion trench 112 and the lower steps 114 of the ribs, then reaches the cushion 23 for buffering, and finally flows onto the test element 50 for testing.

In the present invention, some samples need to be mixed with a buffer solution 60 for slow release before testing. Therefore, the apparatus for collecting and testing a sample further includes a buffer cavity 40 in which the buffer solution 60 is stored, a sealing sheet 70 for sealing the buffer solution in the buffer cavity, and a pipetting cavity 30 hermetically connected to the buffer cavity. The pipetting cavity 30 is used to receive the absorbing element 12 and transfer the buffer solution 60 to the absorbing element 12 and the test cavity 20. In a specific embodiment, the buffer cavity 40 is in threaded connection with the pipetting cavity 30, and a seal is formed between the two. In a specific embodiment, a clip 31 is arranged in the pipetting cavity 30 to fix the collecting component 10 so as to prevent the collecting component 10 from rotating in the pipetting cavity 30 during insertion.

In some embodiments, a sealing gasket 80 is arranged on an outer wall of the bottom of the test cavity 20, the collecting component 10 and the test cavity 20 enter the pipetting cavity 30, and the pipetting cavity contacts an inner wall of the pipetting cavity through the sealing gasket to form a seal.

During use, the collecting component 10 connected to the test cavity 20 is inserted into the pipetting cavity 30; first, the absorbing element 12 of the collecting component is located directly above an opening of the pipetting cavity 30; second, the collecting component 10 continues to move in a direction of insertion into the pipetting cavity 30, and the test cavity 20 enters the pipetting cavity 30 to form a seal; third, the collecting component 10 continues to move in the direction of insertion into the pipetting cavity 30, and the conical lug 115 of the collecting rod contacts the sealing sheet 70; finally, the collecting component 10 continues to move in the direction of insertion into the pipetting cavity 30, the conical lug 115 of the collecting rod reaches the bottom of the buffer cavity, the conical lug 115 of the collecting rod pierces the sealing sheet 70, the absorbing element 12 enters the buffer cavity 40, and the buffer solution 60 enters the absorbing element 12 to be mixed with a sample on the absorbing element 12; and the mixed liquid flows into the test cavity 20 through the absorbing element 12 along the diversion trench 112 of the collecting rod.

A method for collecting and testing a liquid sample by using the apparatus for collecting and testing a sample according to the present invention will be described in detail below.

First, during the production process of the apparatus 100 for collecting and testing a sample, the buffer solution 60 is sealed in the buffer cavity 40, and the sealing sheet 70 is fixed at the opening of the buffer cavity 40; the pipetting cavity 30 is screwed to the buffer cavity 40; the collecting component 10 is connected to the test cavity 20 through the connecting section 117 of the collecting rod, wherein the absorbing element 12 is exposed outside the test cavity 20; and in the initial state, in order to maintain cleanliness and hygiene, the absorbing element 12 is individually packaged in a plastic bag in advance.

Second, the plastic bag on the absorbing element 12 is torn and removed, a sample is collected through the absorbing element 12 (for example, put into the subject's mouth to collect saliva, or put into a container with a collected liquid sample to absorb the sample), and the absorbing element 12 is full of the liquid sample.

Figure 6:
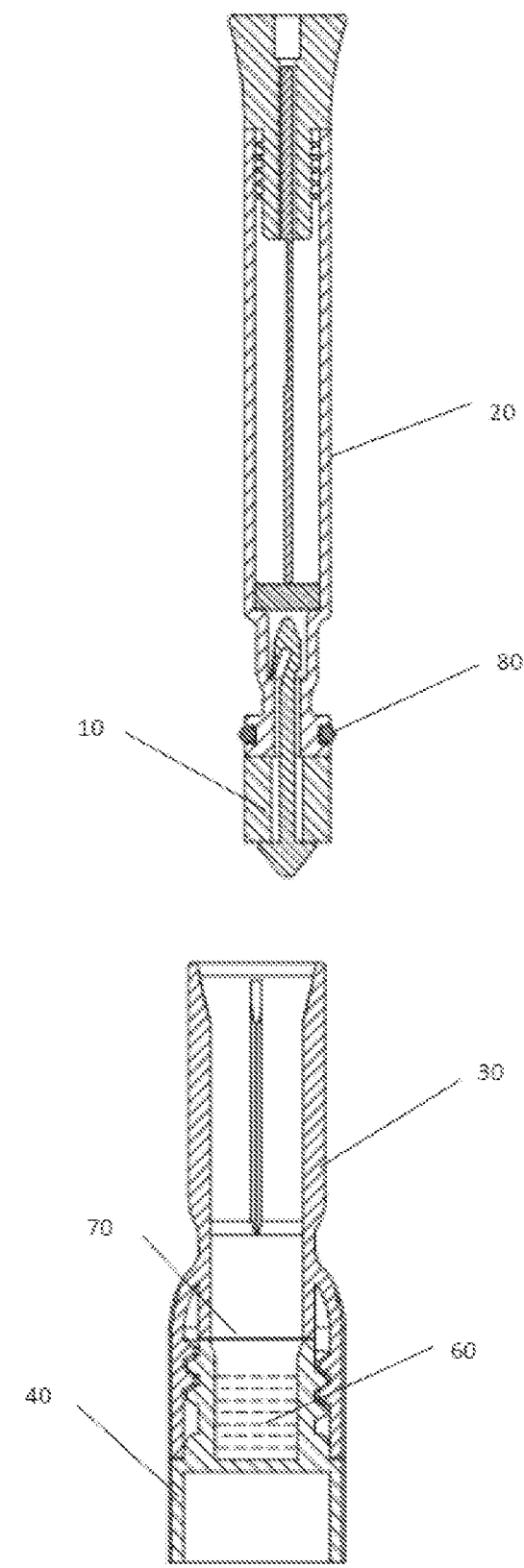
FIG. 6 is a cross-sectional view of the apparatus for collecting and testing a sample according to the present invention before use.

Third, the absorbing element 12 of the collecting component full of the liquid sample is placed directly above the opening of the pipetting cavity 30, and then the collecting component 10 and the test cavity 20 connected to the collecting component 10 are inserted into the pipetting cavity 30 through the collecting end 18, as shown in FIG. 6.

Fourth, the collecting component 10 moves in the pipetting cavity 30 in the direction of insertion into the pipetting cavity 30. After the sealing gasket 80 on the outer wall of the test cavity 20 reaches the pipetting cavity 30, the pipetting cavity 30 is sealed, as shown in FIG. 7.

Figure 7:
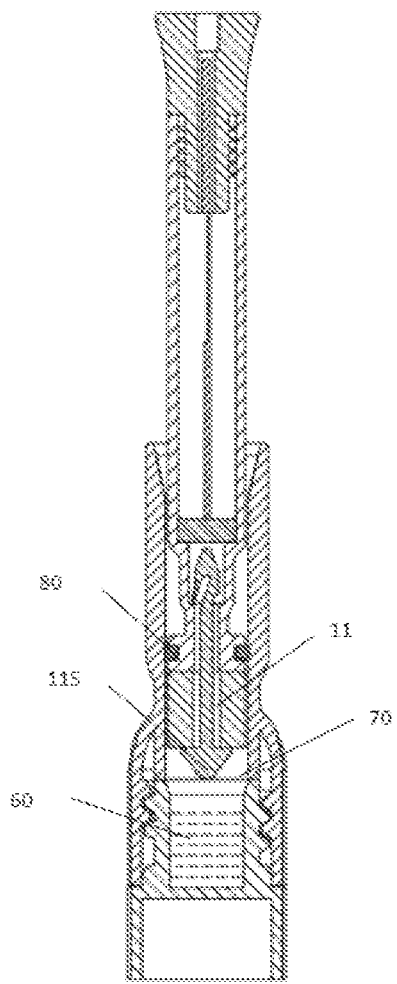
FIG. 7 is a cross-sectional view showing that the collecting component of the apparatus for collecting and testing a sample according to the present invention reaches a buffer cavity.

Fifth, the collecting component 10 continues to move in the pipetting cavity 30 in the direction of insertion into the pipetting cavity 30 until the conical lug 115 of the collecting component reaches the sealing sheet 70, as shown in FIG. 7.

Figure 8:
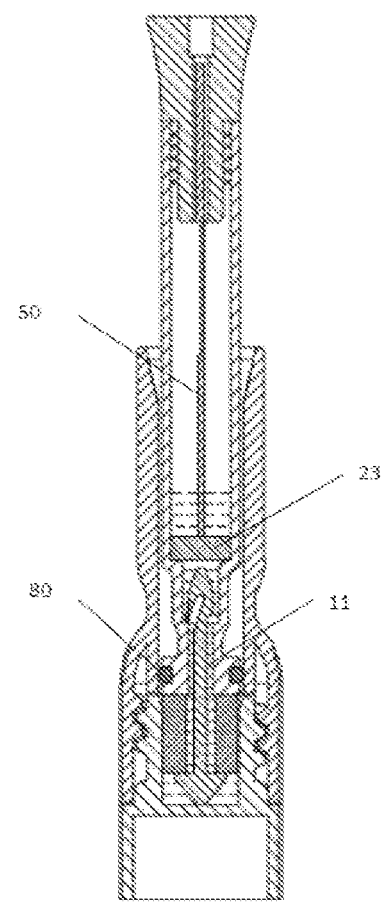
FIG. 8 is a cross-sectional view showing that the collecting component of the apparatus for collecting and testing a sample according to the present invention reaches the buffer cavity and the sample is buffered and tested.

Sixth, the collecting component 10 and the test cavity 20 continue to move in the same direction, the conical lug 115 of the collecting component pierces the sealing sheet 70 on the buffer cavity, the buffer cavity 40 is communicated with the pipetting cavity 30 to form a sealed cavity, the collecting component 10 continues to move and enters the buffer cavity 40, the sealed cavity formed by the buffer cavity 40 and the pipetting cavity 30 becomes small, the pressure in the cavity increases, and the buffer solution 60 is squeezed onto the absorbing element 12 and mixed with the sample on the absorbing element 12; meanwhile, because the pressure in the sealed cavity greater than the pressure (equivalent to atmospheric pressure) in the test cavity 20, the mixed liquid flows into the test cavity 20 along the absorbing element 12, the diversion trench 112 of the collecting rod and the lower steps 114 of the ribs, as shown in FIG. 8.

Seventh, after the liquid entering the test cavity 20 reaches the cushion 23, the liquid is absorbed and buffered by the cushion 23, and then flows onto the test element 50 in contact with the cushion 23 for testing, as shown in FIG. 8.

Eighth, the test result on the test element 50 is read to complete the test.

What is claimed is:

1. An apparatus for collecting and testing a sample, comprising:
   a test cavity and a collecting component, wherein the test cavity is connected to the collecting component and the test cavity and the collecting component are in a liquid communication;
   an inner wall of the test cavity is provided with a first step, the collecting component comprises a collecting rod and an absorbing element sleeved on the collecting rod;
   a connecting end of the collecting rod is provided with a barb, and a tail end of the barb is tapered; and
   the barb at the connecting end of the collecting rod is clamped to the first step to connect the test cavity with the collecting component.

2. The apparatus according to claim 1, wherein the connecting end of the collecting rod of the collecting component is inserted into the test cavity from a bottom of the test cavity, the tail end of the barb at the connecting end of the collecting rod enters the test cavity, then an open end of the barb is compressed, and the barb and the connecting end enter the test cavity; and
   after the open end of the barb reaches the first step, because an inner diameter of the test cavity increases, the open end of the barb rebounds to restore to an original shape, and the barb is clamped to the first step.

3. The apparatus according to claim 2, wherein the collecting rod is provided with at least two ribs, and a diversion trench is formed between the at least two ribs; and
   a liquid on the absorbing element is communicated with the test cavity through the diversion trench.

4. The apparatus according to claim 3, wherein each rib of the at least two ribs is of a stepped structure; and the absorbing element is located on an upper step.

5. The apparatus according to claim 3, further comprising a cover, wherein the cover covers the test cavity, and a clamping groove for accommodating a test element is provided in the cover.

6. The apparatus according to claim 5, wherein the inner wall of the test cavity is further provided with a second step above the first step.

7. The apparatus according to claim 6, further comprises a cushion; and the cushion is located on the second step.

8. The apparatus for collecting and testing a sample according to claim 7, wherein the liquid entering the test cavity through the diversion trench of the collecting rod flows into the cushion, and then the liquid flows from the cushion to the test element.

9. The apparatus according to claim 5, further comprising a buffer cavity, a sealing sheet for sealing the buffer cavity, and a pipetting cavity hermetically connected to the buffer cavity; wherein
a buffer solution is sealed in the buffer cavity.

10. The apparatus according to claim 9, wherein a sealing gasket is arranged on an outer wall of the bottom of the test cavity, and the collecting component and the test cavity enter the pipetting cavity to form a seal between the test cavity and the pipetting cavity.

11. The apparatus according to claim 10, wherein the collecting component connected to the test cavity is inserted into the pipetting cavity;

first, the absorbing element of the collecting component is located directly above an opening of the pipetting cavity;

second, the collecting component continues to move in a direction of insertion into the pipetting cavity, and the test cavity enters the pipetting cavity to form the seal;

third, the collecting component continues to move in the direction of insertion into the pipetting cavity, and a conical lug of the collecting rod contacts the sealing sheet;

finally, the collecting component continues to move in the direction of the insertion into the pipetting cavity, the conical lug of the collecting rod reaches a bottom of the buffer cavity, the conical lug of the collecting rod pierces the sealing sheet, the absorbing element enters the buffer cavity, and the buffer solution enters the absorbing element to be mixed with a sample on the absorbing element to obtain a mixed liquid; and the mixed liquid flows into the test cavity through the absorbing element along the diversion trench of the collecting rod.

12. The apparatus according to claim 2, wherein a conical lug is provided on the collecting rod adjacent to a collecting end of the absorbing element.

* * * * *